(12) United States Patent
Sgroi, Jr.

(10) Patent No.: US 11,166,728 B2
(45) Date of Patent: Nov. 9, 2021

(54) RELOAD ASSEMBLY FOR A CIRCULAR STAPLING DEVICE

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 111 days.

(21) Appl. No.: 16/739,697

(22) Filed: Jan. 10, 2020

(65) Prior Publication Data

US 2020/0253609 A1 Aug. 13, 2020

Related U.S. Application Data

(60) Provisional application No. 62/802,749, filed on Feb. 8, 2019.

(51) Int. Cl.
*A61B 17/115* (2006.01)
*A61B 17/072* (2006.01)
*A61B 17/00* (2006.01)

(52) U.S. Cl.
CPC ... *A61B 17/1155* (2013.01); *A61B 2017/0053* (2013.01); *A61B 2017/07271* (2013.01); *A61B 2017/07285* (2013.01)

(58) Field of Classification Search
CPC .................. A61B 17/1155; A61B 2017/07285
USPC ...................................... 227/180.1
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |

(Continued)

FOREIGN PATENT DOCUMENTS

| CA | 908529 A | 8/1972 |
|---|---|---|
| CA | 2805365 A1 | 8/2013 |

(Continued)

OTHER PUBLICATIONS

European Search Report dated Jun. 22, 2020, issued in EP Appln. No. 20156169, 12 pages.

*Primary Examiner* — Gloria R Weeks (57) ABSTRACT

A reload assembly includes a shell housing, a knife carrier, and at least one engagement member. The shell housing includes an inner housing portion and an outer housing portion that is spaced from the outer housing portion to define an annular cavity. The knife carrier defines a longitudinal axis and supports a knife. The knife carrier also defines a stepped central bore having a distal portion and a proximal portion and has a shoulder positioned between the distal and proximal portions. The at least one engagement member is supported on the knife carrier and is positioned to engage the inner housing portion of the shell housing when the knife carrier is in its retracted position to retain the knife carrier in the retracted position.

17 Claims, 8 Drawing Sheets

(56) References Cited

U.S. PATENT DOCUMENTS

| | | |
|---|---|---|
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A * | 9/1990 | Lipatov ............... A61B 17/115 227/180.1 |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |

(56) References Cited

U.S. PATENT DOCUMENTS

| | | |
|---|---|---|
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |

(56) References Cited

U.S. PATENT DOCUMENTS

| | | |
|---|---|---|
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,573,464 B2 * | 11/2013 | Nalagatla ........... A61B 17/1155 227/179.1 |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 10,405,864 B2 * | 9/2019 | Zhan ................ A61B 17/1155 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0278346 A1 * | 11/2011 | Hull ................ A61B 17/1155 227/180.1 |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |

(56) References Cited

U.S. PATENT DOCUMENTS

| | | |
|---|---|---|
| 2013/0175319 A1 | 7/2013 | Felder et al. |
| 2013/0175320 A1 | 7/2013 | Mandakolathur Vasudevan et al. |
| 2013/0181035 A1* | 7/2013 | Milliman ............ A61B 17/068 227/180.1 |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2015/0173757 A1* | 6/2015 | Williams ............ A61B 17/1155 227/180.1 |
| 2016/0000428 A1* | 1/2016 | Scirica ............ A61B 1/00089 227/180.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2614785 A2 | 7/2013 |
| EP | 2623042 A2 | 8/2013 |
| EP | 3412225 A1 | 12/2018 |
| EP | 3649966 A1 | 5/2020 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

RELOAD ASSEMBLY FOR A CIRCULAR STAPLING DEVICE

CROSS-REFERENCE TO RELATED APPLICATIONS

This application claims the benefit of and priority to U.S. Provisional Patent Application Ser. No. 62/802,749 filed Feb. 8, 2019, the entire disclosure of which is incorporated by reference herein.

BACKGROUND

1. Technical Description

The present disclosure is directed to circular stapling devices and, more particularly, to reload assemblies for circular stapling devices with structure to retain a knife carrier in a retracted position prior to and after firing of the stapling device.

2. Background of Related Art

Conventional circular stapling devices include an elongate body and a shell or reload assembly supported on a distal portion of the elongate body. The reload assembly includes a shell housing, a staple cartridge supported on the shell housing having a plurality of staples, a pusher assembly, a knife defining a cylindrical cavity, and a knife carrier that supports the knife and is movable through the staple cartridge to core tissue. The pusher assembly includes an annular pusher and a staple pushing member that is engaged with the annular pusher and is movable to move the staple pushing member to eject staples from the staple cartridge.

After a stapling device has been operated to staple and cut tissue, the knife carrier and the knife are retracted to withdraw the knife into the shell housing. This serves two purposes. The first is that the knife is moved to a position to allow removal of a tissue donut from within the cavity defined by the knife. The second is to position the knife in a location recessed within the shell housing to avoid injury to a clinician during manipulation and disposal of the reload assembly.

A continuing need exists in the art for a reload assembly that includes improved structure for retaining the knife/knife carrier in a retracted position.

SUMMARY

One aspect of the present disclosure is directed to a reload assembly including a shell housing, a staple cartridge, a pusher assembly, a knife carrier, and at least one engagement member. The shell housing includes an inner housing portion and an outer housing portion. The inner housing portion is spaced from the outer housing portion to define an annular cavity. The staple cartridge is supported on a distal portion of the shell housing and has a plurality of staple pockets each receiving a staple. The pusher assembly is supported within the annular cavity and is movable between a retracted position and an advanced position to eject the staples from the staple cartridge. The knife carrier defines a longitudinal axis and supports a knife. The knife carrier defines a stepped central bore having a distal portion and a proximal portion and has a shoulder positioned between the distal and proximal portions. The at least one engagement member is supported on the knife carrier and is positioned to engage the inner housing portion of the shell housing when the knife carrier is in its retracted position to retain the knife carrier in the retracted position until a predetermined force is applied to the knife carrier to disengage the engagement member from the inner housing portion.

In embodiments, the inner housing portion of the shell housing has an outer surface defining at least one recess and the at least one engagement member is received within the at least one recess when the knife carrier is in its retracted position.

In some embodiments, the at least one engagement member includes a carrier spring that is supported on the shoulder of the knife carrier and extends across a portion of the stepped central bore, wherein the carrier spring is received within the at least one recess when the knife carrier is in its retracted position.

In certain embodiments, the at least one recess includes two recesses and the at least one engagement member includes two carrier springs, wherein each of the carrier springs is received in a respective one of the two recesses when the knife carrier is in its retracted position.

In embodiments, the at least one recess defines a distal wall that defines a wall axis, wherein the wall axis and the longitudinal axis of the knife carrier define an angle $\Omega$ of between 45 degrees and 85 degrees.

In some embodiments, the angle $\Omega$ is between 60 degrees and 75 degrees.

In certain embodiments, the shoulder defines openings and the carrier spring includes first and second ends, wherein each of the first and second ends is positioned within one of the openings to secure the carrier spring to the shoulder of the knife carrier.

In embodiments, the pusher assembly includes an annular pusher and a pushing member, wherein the pushing member includes fingers that are received within the staple pockets of the staple cartridge.

Another aspect of the present disclosure is directed to a circular stapling device including an elongated body and a reload assembly. The elongated body has a proximal portion and a distal portion. The reload assembly is supported on the distal portion of the elongated body and includes a shell housing, a staple cartridge, a pusher assembly, a knife carrier, and at least one engagement member. The shell housing includes an inner housing portion and an outer housing portion. The inner housing portion is spaced from the outer housing portion to define an annular cavity. The staple cartridge is supported on a distal portion of the shell housing and has a plurality of staple pockets that receive staples. The pusher assembly is supported within the annular cavity and is movable between a retracted position and an advanced position to eject the staples from the staple cartridge. The knife carrier defines a longitudinal axis and supports a knife. The knife carrier also defines a stepped central bore having a distal portion and a proximal portion and includes a shoulder positioned between the distal and proximal portions of the central bore. The at least one engagement member is supported on the knife carrier and is positioned to engage the inner housing portion of the shell housing when the knife carrier is in its retracted position to retain the knife carrier in its retracted position until a predetermined force is applied to the knife carrier.

In some embodiments, the circular stapling device includes a handle assembly, wherein the elongated body being supported on the handle assembly.

In certain embodiments, the elongated body is adapted to be coupled to a robotic system.

BRIEF DESCRIPTION OF THE DRAWINGS

Various embodiments of the presently disclosed reload assembly are described herein below with reference to the drawings, wherein.

DETAILED DESCRIPTION OF EMBODIMENTS

The presently disclosed reload assembly will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Figures 1, 2:
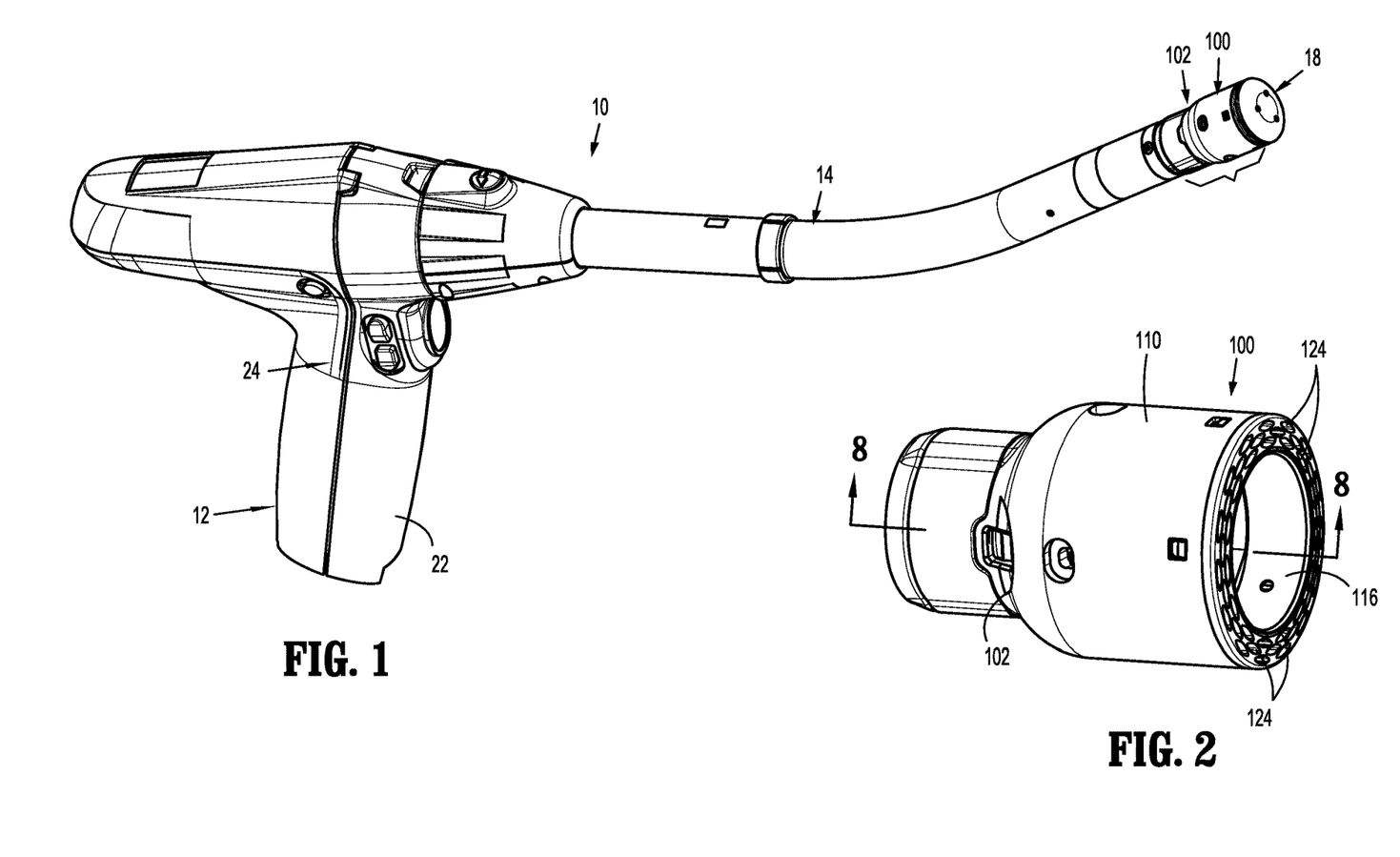
FIG. 1 is a side perspective view of a circular stapling device including an exemplary embodiment of the presently disclosed reload assembly in accordance with the present disclosure.
FIG. 2 is a side perspective view of the reload assembly of FIG. 1.

FIGS. 1 and 2 illustrate a circular stapling device 10 including an exemplary embodiment of the presently disclosed reload assembly shown generally as reload assembly 100. The stapling device 10 includes a handle assembly 12, an elongate body or adaptor assembly 14, the reload assembly 100, and an anvil assembly 18 that is supported for movement in relation to the reload assembly 100 between spaced and approximated positions as is known in the art. The reload assembly 100 includes a proximal portion 102 (FIG. 1) that is releasably coupled to a distal portion 14a of the elongate body 14. The handle assembly 12 includes a stationary grip 22 that supports actuation buttons 24 for controlling operation of various functions of the stapling device 10 including approximation of the reload and anvil assemblies 100 and 18, respectively, firing of staples from the reload assembly 100, and cutting or coring of tissue.

The stapling device 10 is illustrated as an electrically powered stapling device including an electrically powered handle assembly 12 that may support one or more batteries (not shown). The elongate body 14 is in the form of an adaptor assembly that translates power from the handle assembly 12 to the reload and anvil assemblies 100, 18, respectively. Examples of electrically powered stapling devices can be found in U.S. Pat. No. 9,055,943 (the '943 patent), U.S. Pat. No. 9,023,014 (the '014 patent), and U.S. Publication Nos. 2018/0125495, and 2017/0340351 which are incorporated herein by reference in their entirety. Alternately, it is envisioned that the present disclosure could also be incorporated into a manually powered stapling device such as taught in U.S. Pat. No. 7,303,106 (the '106 patent) or a stapling device that is configured for use with a robotic system that does not include a handle assembly. The '106 patent is also incorporated herein by reference in its entirety.

Figure 3:
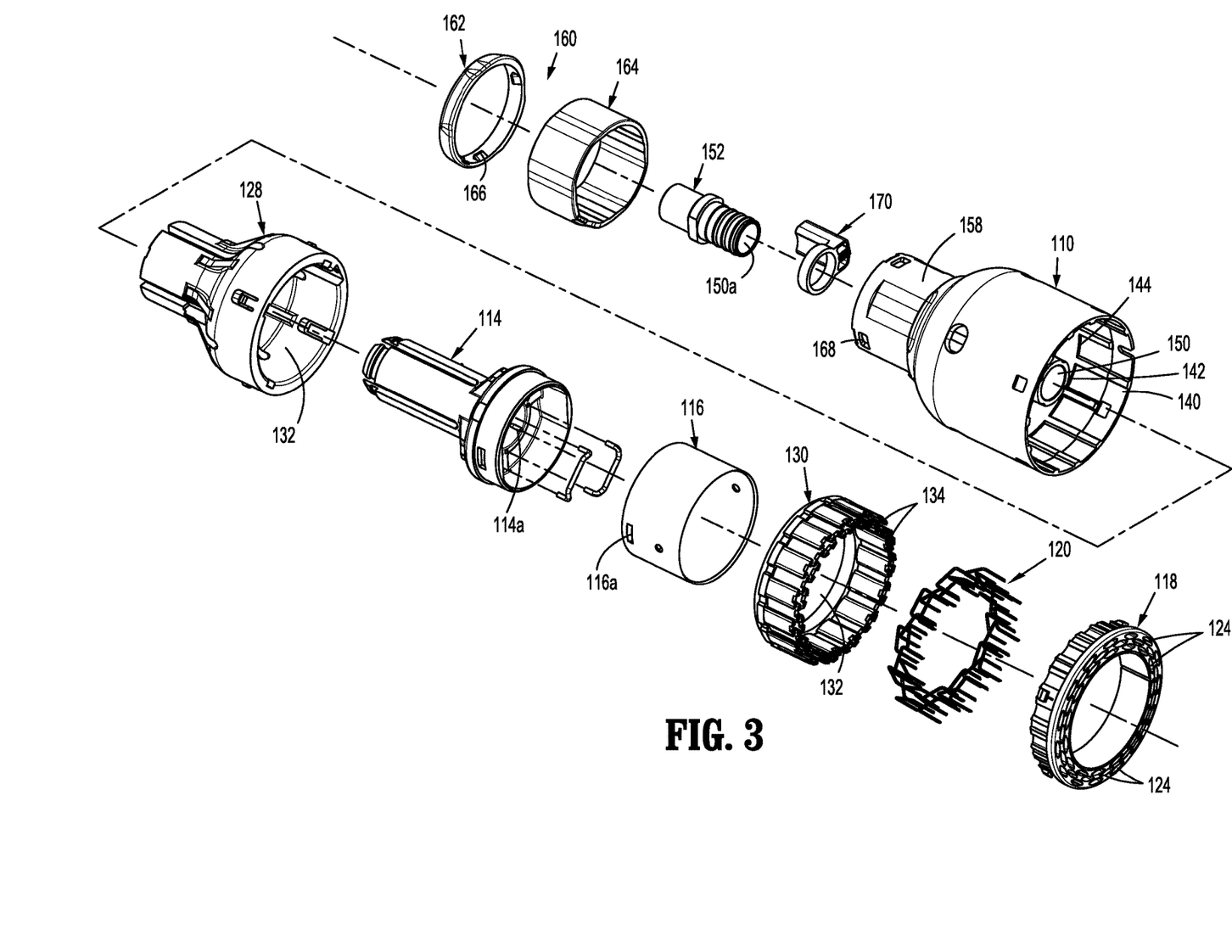
FIG. 3 is an exploded side perspective view of the reload assembly of FIG. 2.

Referring to FIGS. 2 and 3, the reload assembly 100 includes a shell housing 110, a pusher assembly 112 (FIG. 8), a knife carrier 114, an annular knife 116 supported on the knife carrier 114, a staple cartridge 118, and a plurality of staples 120 supported within the staple cartridge 118. The staple cartridge 118 is annular and defines annular rows of staple pockets 124. Each of the staple pockets 124 supports one of the plurality of staples 120. The pusher assembly 112 includes an annular pusher 128 and a staple pushing member 130 that together define a longitudinal through bore 132. The pusher 128 has a distal portion that abuts a proximal portion of the staple pushing member 130 such that distal movement of the pusher 128 within the shell housing 110 causes distal movement of the staple pushing member 130 within the shell housing 110. The staple pushing member 130 of the reload 100 has a plurality of fingers 134. Each of the plurality of fingers 134 is received within a respective one of the staple pockets 124 of the staple cartridge 118 and is movable through the respective staple pocket 124 to eject the staples 120 from the staple pockets 124 when the staple pushing member 130 is moved from a retracted position to an advanced position within the shell housing 110.

The shell housing 110 includes an outer housing portion 140 and an inner housing portion 142 that are spaced from each other to define an annular cavity 144. The pusher assembly 112 (FIG. 8), the knife carrier 114, and the annular knife 116 are movable within the annular cavity 144 between retracted and advanced positions. The pusher assembly 112 is movable from its retracted position to its advanced position independently of the knife carrier 114 and annular knife 116 to eject the staples 120 from the staple cartridge 118. The annular knife 116 is supported about an outer surface of the knife carrier 114 and defines a cylindrical cavity 117. In embodiments, the knife 116 includes projections 116a that are received openings 116b on the knife carrier 114 to secure the knife 116 about the knife carrier 114. Alternately, other fastening techniques may be used to secure the knife 116 to the knife carrier 114. After the pusher assembly 112 is moved from its retracted position to its advanced position, the knife carrier 114 can be moved from its retracted position to its advanced position to cut tissue positioned radially inward of the staple cartridge 118.

Figure 6:
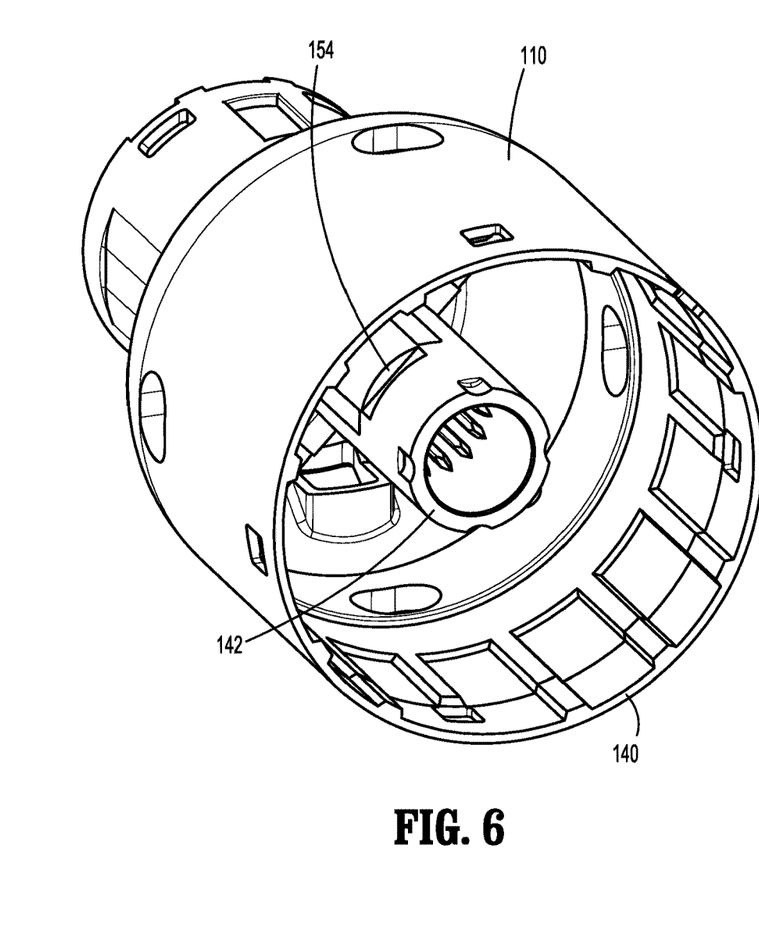
FIG. 6 is a perspective view from the distal end of the shell housing of the reload assembly shown in FIG. 3.

The inner housing portion 142 of the shell housing 110 defines a through bore 150 (FIG. 3) that receives an anvil shaft (not shown) of an anvil assembly 18 (FIG. 1). For a more detailed description of the anvil assembly, see, e.g., the '106 patent. The through bore 150 receives a bushing 152 that defines a through bore 150a that is coaxial with the through bore 150. In embodiments, the bushing 152 is formed of a high strength material, e.g., metal, to provide added strength to the inner housing portion 142 of the shell housing 110. The inner housing portion 142 includes an outer surface that defines one or more recesses 154 (FIG. 6).

The shell housing 110 includes a proximal portion 158 (FIG. 3) that supports a coupling mechanism 160 that is operable to couple the reload assembly 100 to the adaptor assembly 14 of the stapling device 10 (FIG. 1). The coupling mechanism 160 includes a retaining member 162 and a coupling member 164. The coupling member 164 is received about the proximal portion 158 of the shell housing 110 and is configured to engage a distal end of the adaptor assembly 14 to couple the adaptor assembly 14 to the reload assembly 100. In embodiments, the retaining member 162 includes projections 166 that are received in openings 168 in the proximal portion 158 of the shell housing 110 to secure the retaining member 162 and the coupling member 164 to the shell housing 100. It is envisioned that other coupling mechanisms can be used to secure the reload assembly 100 to the adaptor 14.

The reload assembly 100 may include an e-prom 170 that is supported on the shell housing 110. As is known in the art, the e-prom can communicate with the adaptor assembly 14 to provide information to the adaptor assembly 14 and handle assembly 12 related to characteristics of the reload assembly 10.

Figures 4, 5:
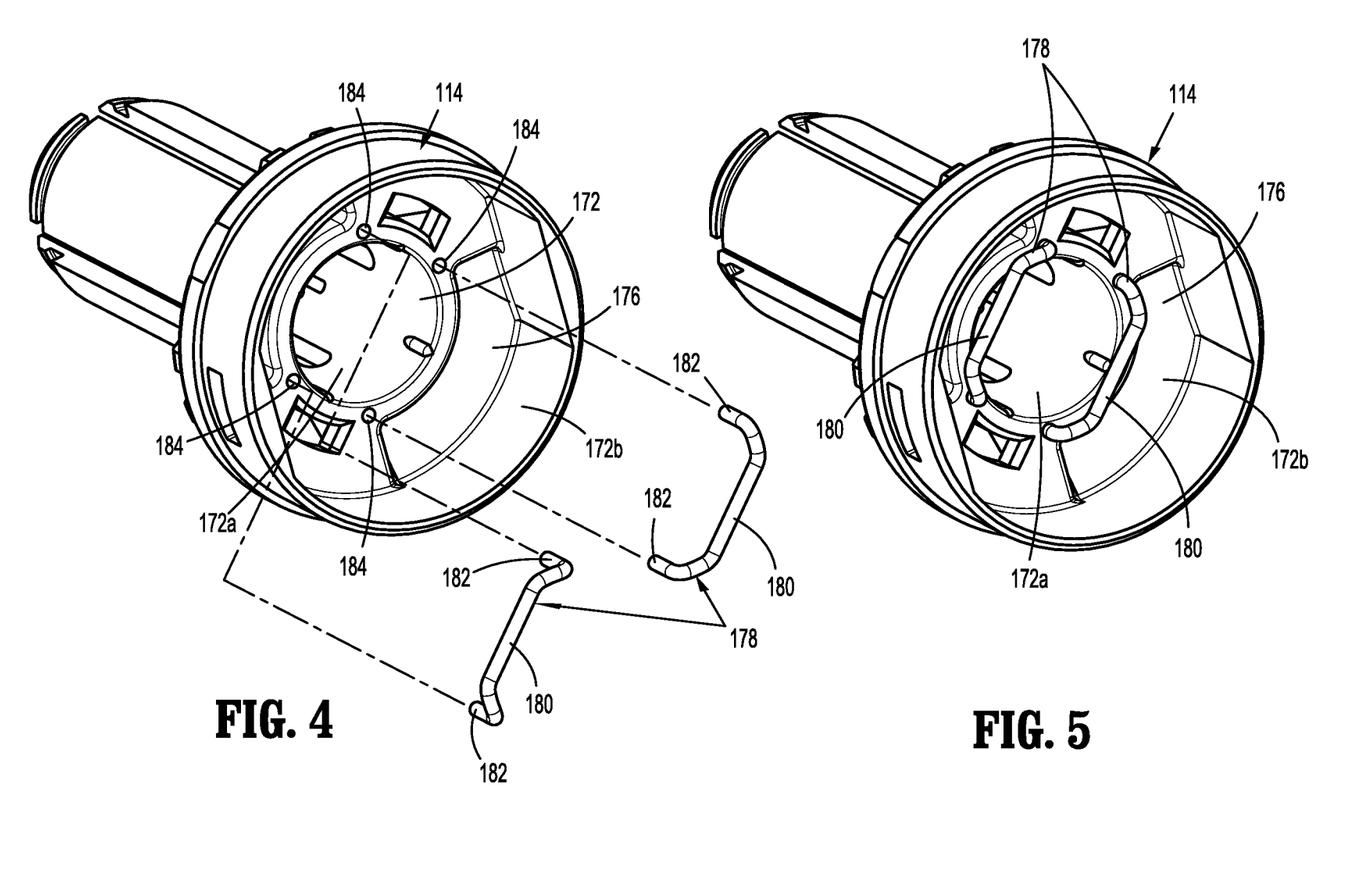
FIG. 4 is a perspective view from the distal end of a knife carrier of the reload assembly shown in FIG. 3 with carrier springs separated from a body of the knife carrier.
FIG. 5 is a perspective view from the distal end of the knife carrier of shown in FIG. 4 with the carrier springs secured to the body of the knife carrier.
Figure 8:
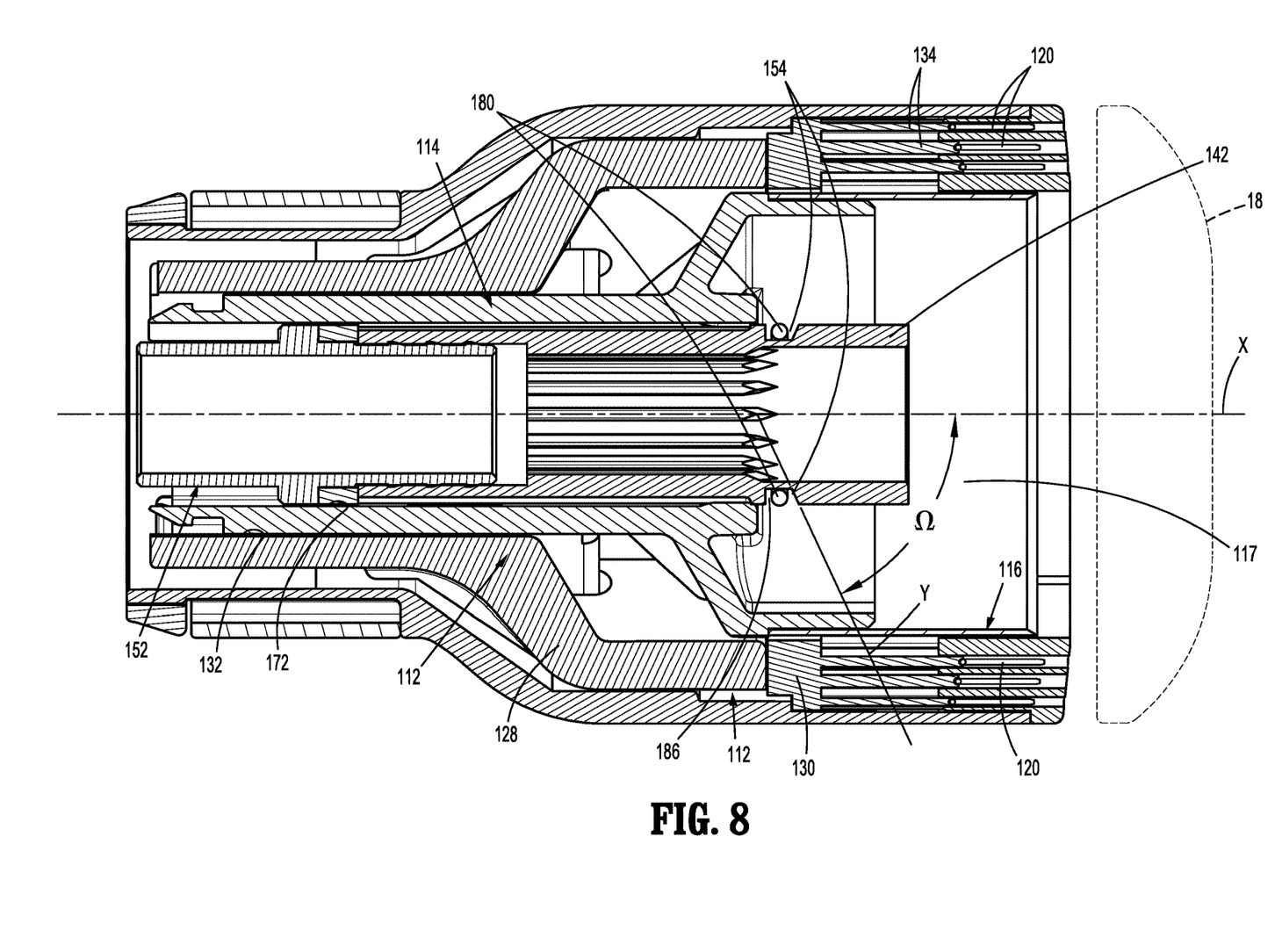
FIG. 8 is a cross-sectional view taken along section line 8-8 of FIG. 2 with the reload assembly in a pre-fired position.

Referring to FIGS. 4 and 5, the knife carrier 114 is movably positioned within the through bore 132 FIG. 8) of the pushing assembly 112 between its retracted and advanced positions and defines a stepped central bore 172. The stepped central bore 172 includes a small diameter proximal portion 172a and a larger diameter distal portion 172b. The proximal portion 172a of the central bore 172 of the knife carrier 114 receives the inner housing portion 142 (FIG. 8) of the shell housing 110 such that the knife carrier 114 is slidable about the inner housing portion 142.

The knife carrier 114 defines an annular shoulder 176 that is positioned between the proximal portion 172a and the distal portion 172b of the central bore 172. The shoulder 176 supports at least one engagement member 178 that extends across a portion of the central bore 172. The at least one engagement member 178 is positioned to be received within a respective one of the recesses 154 (FIG. 7) of the inner housing portion 142 of the shell housing 110 when the knife carrier 114 is in its retracted position to retain the knife carrier 114 in its retracted position as described in further detail below.

In embodiments, the at least one engagement member 178 includes two carrier springs 180. Each of the carrier springs 180 is formed of a resilient material, e.g., spring steel, and is supported on an opposite side of the shoulder 176. The carrier springs 180 extend across opposite sides of the central bore 172 of the inner housing portion 142. In embodiments, opposite ends 182 (FIG. 4) of each of the carrier springs 180 are received in openings 184 (FIG. 4) defined in the annular shoulder 176 of the knife carrier 114 to secure the carrier springs 180 to the knife carrier 114. It is envisioned that the at least one engagement member 78 may include one or more carrier springs 180, e.g., 1, 2, 3, etc.

Figure 7:
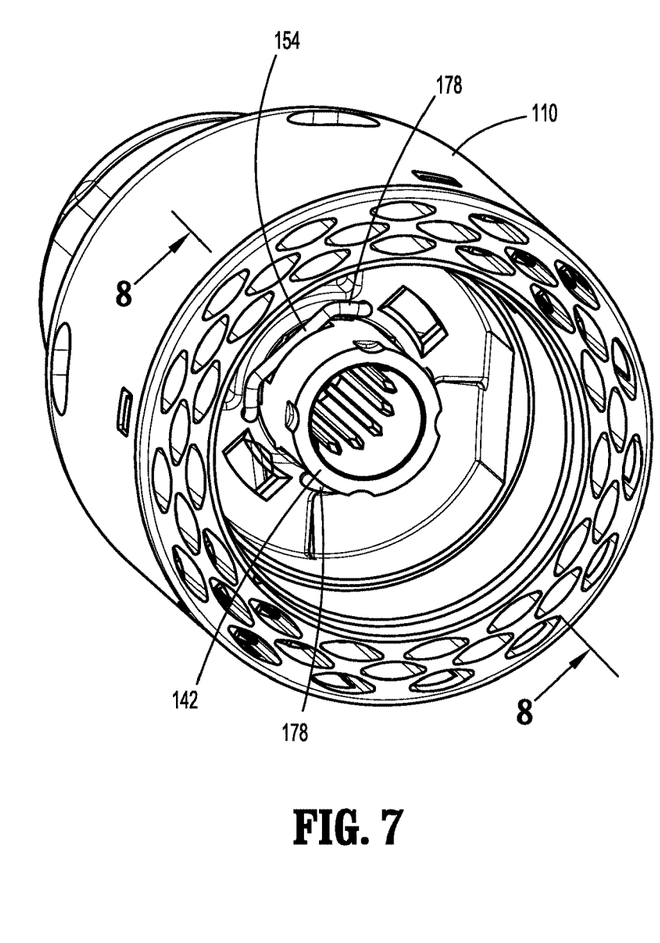
FIG. 7 is a perspective view from the distal end of the shell housing and staple cartridge of the reload assembly shown in FIG. 3 with the staple cartridge supported on the distal end of the shell housing.

Referring to FIGS. 6-8, the inner housing portion 142 of the shell housing 110 includes two recesses 154. Each one of the recesses 154 is aligned with a respective one of the carrier springs 180 and is positioned to receive the carrier spring 180 when the knife carrier 114 is in its retracted position. The shell housing 110 defines a longitudinal axis "X" (FIG. 8). Each of the recesses 154 is defined by a distal wall 186 that defines an axis "Y". In embodiments, the longitudinal axis "X" of the knife carrier and the axis "Y" of the distal wall 186 define an angle Ω (FIG. 8). In embodiments, Ω is from about 45 degrees and 85 degrees. In other embodiments, is from about 60 and about 75 degrees. The angle of the distal wall 186 is selected such that the distal wall 186 obstructs movement of the carrier springs 180 from the recesses 154 to obstruct movement of the knife carrier 114 from its retracted position towards its distal position until a predetermined force is applied to the knife carrier 114. The predetermined force should exceed the force required to remove a tissue donut from the cavity 117 (FIG. 8) defined by the cylindrical knife 116.

Figure 9:
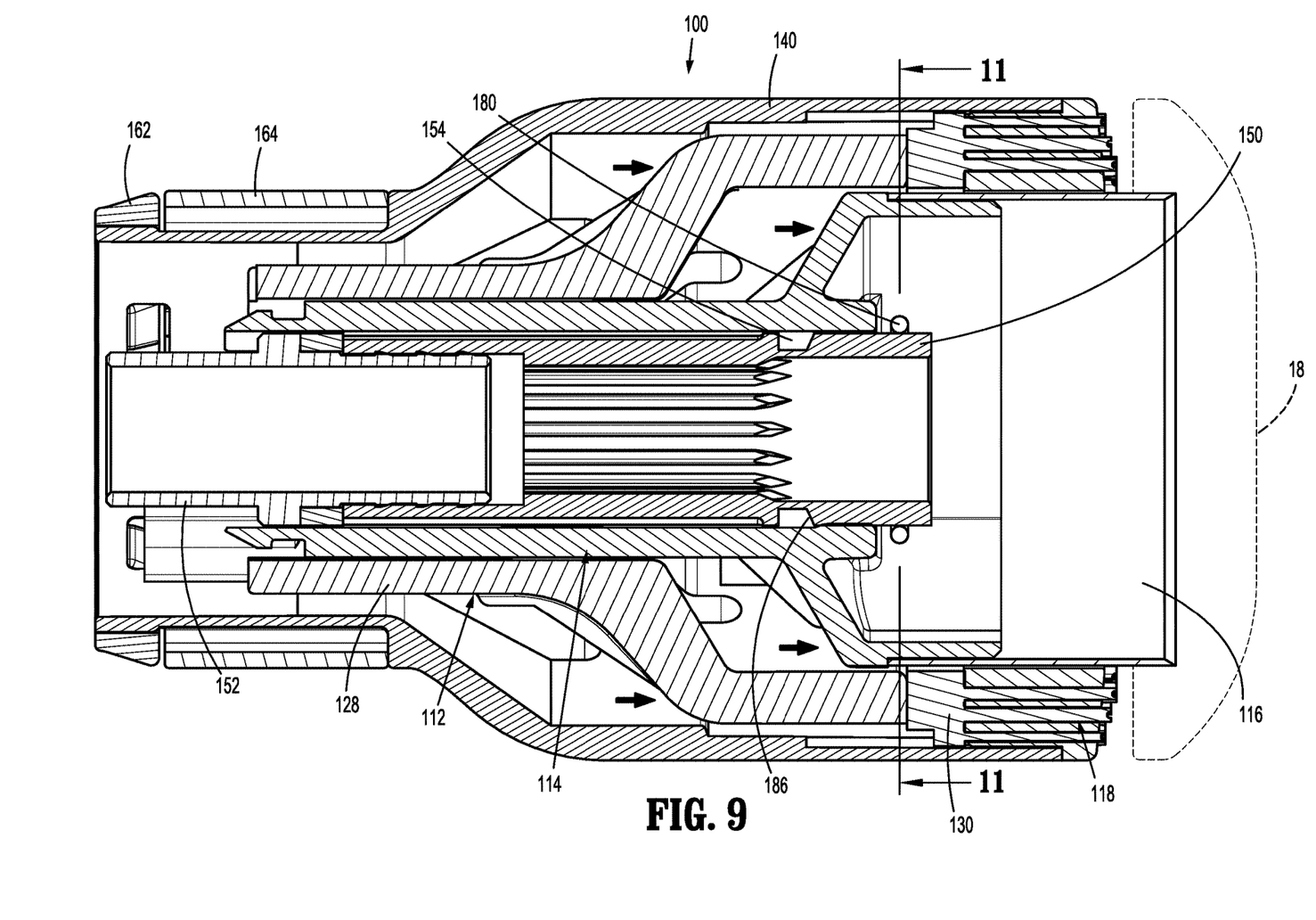
FIG. 9 is a cross-sectional view taken along section line 8-8 of FIG. 2 with the reload assembly in a fired position.
Figure 10:
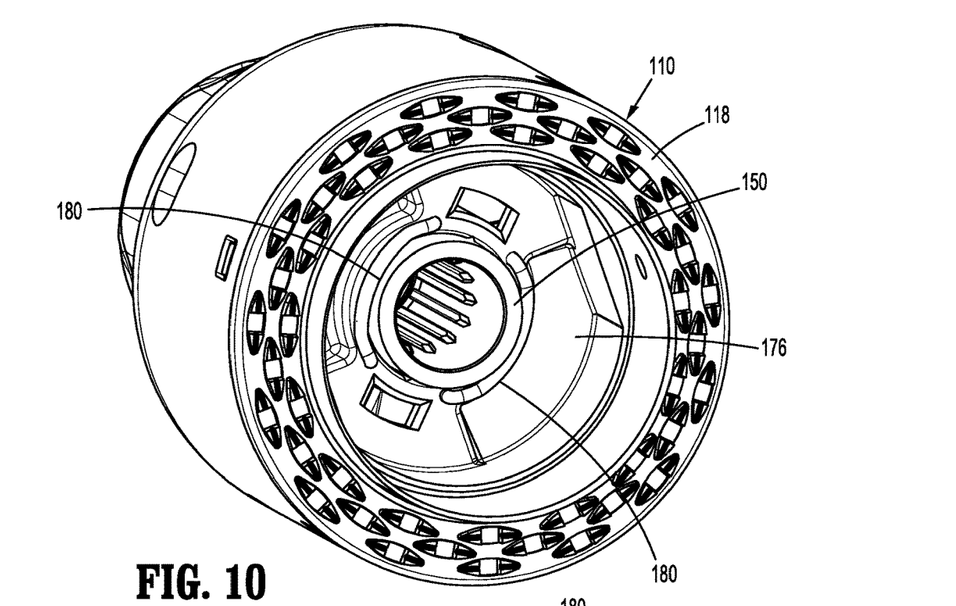
FIG. 10 is a perspective view from the distal end of the reload assembly shown in FIG. 9 after the reload assembly is fired.
Figure 11:
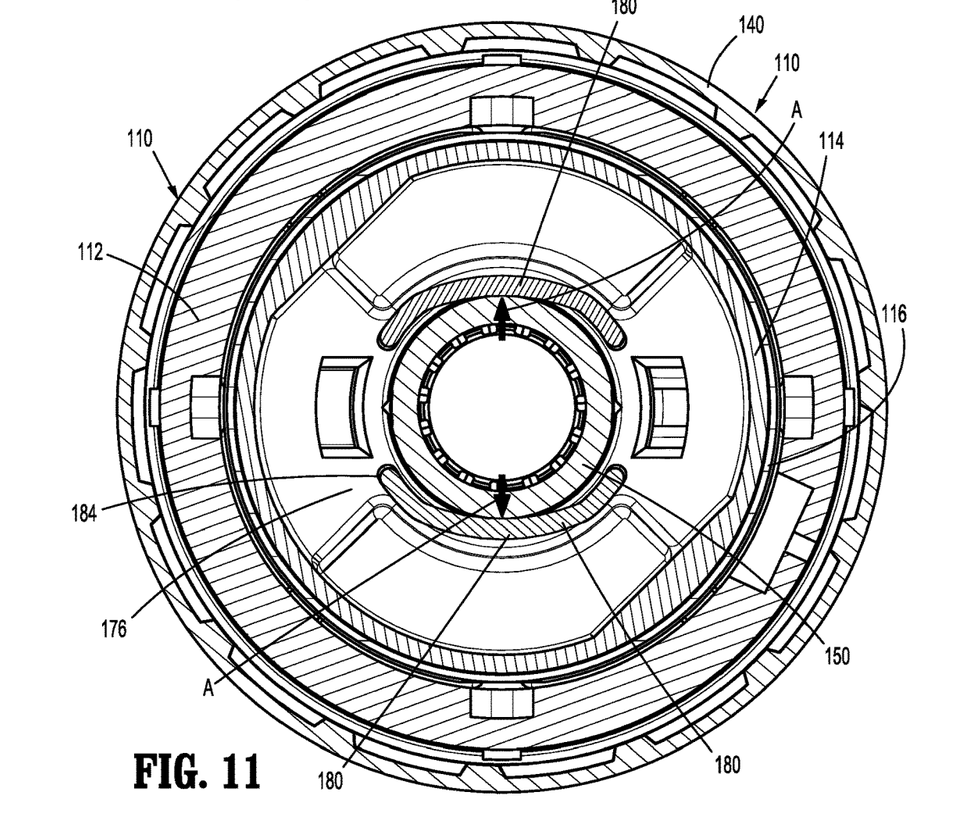
FIG. 11 is a cross-sectional view taken along section line 11-11 of FIG. 9.

Referring to FIGS. 9-11, when the adaptor 14 is actuated to advance the knife carrier 114 from the retracted position towards its advanced position, the distal walls 186 of the recesses 154 of the inner housing portion 142 engages the carrier springs 180 to urge the carrier springs 180 outwardly from the recesses 154 such that the knife carrier 114 is advanced about the inner housing portion 142 of the shell housing 110. As the knife carrier 114 moves towards its advanced position, the carrier springs 180 are biased outwardly in the direction indicated by arrows "A" in FIG. 11 and slide along the outer surface of the inner housing portion 142 of the shell housing 110.

Figure 12:
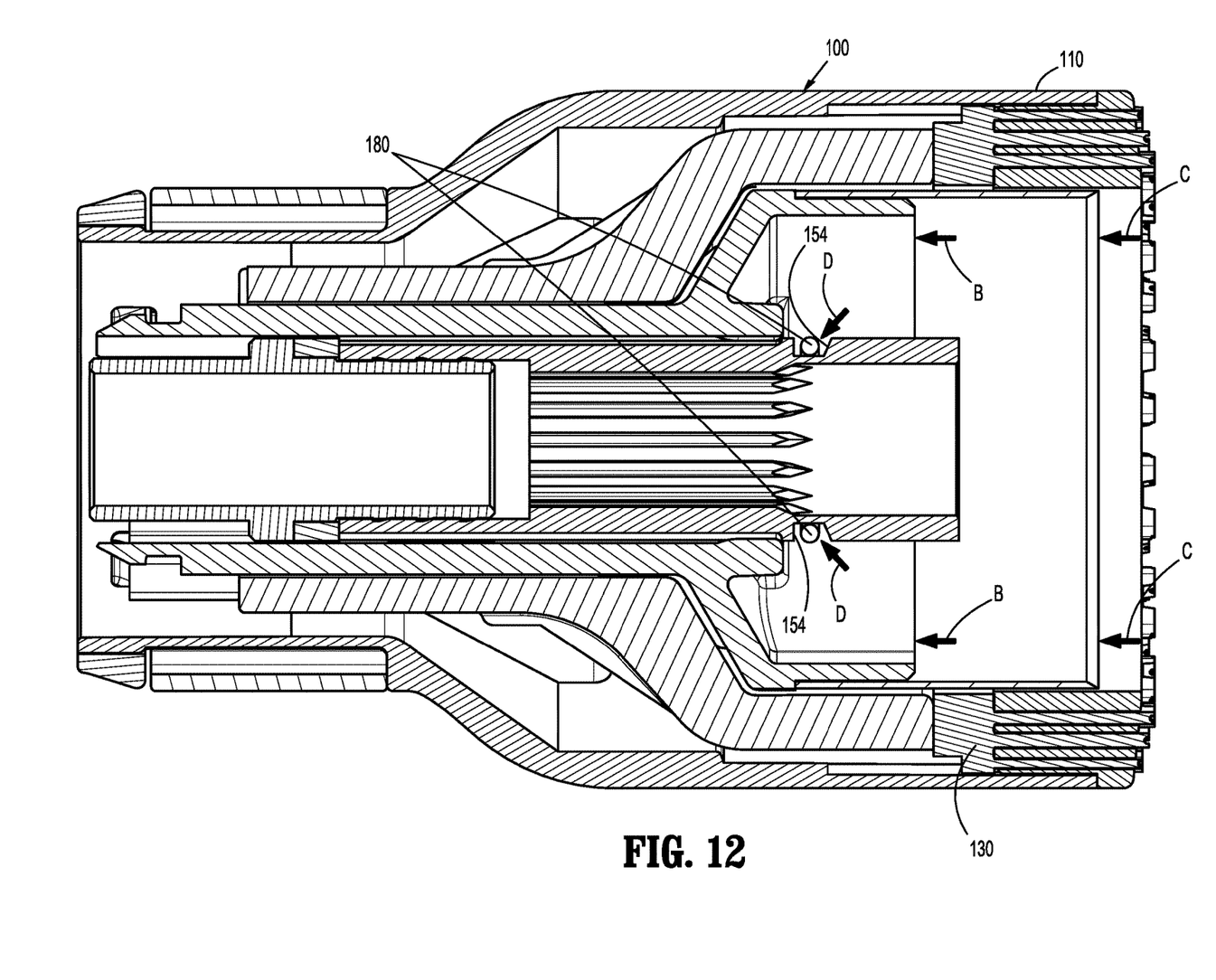
FIG. 12 is a cross-sectional view taken along section line 8-8 of FIG. 2 after the reload assembly has been fired with the knife carrier and knife in a retracted position.

Referring to FIG. 12, when the knife carrier 114 is returned to its retracted position in the direction indicated by arrows "B", the annular knife 116 moves in the direction indicated by arrows "C" to a position recessed within the shell housing 110, and the carrier springs 180 flex inwardly in the direction indicated by arrows "D" into the recesses 154 in the inner housing portion 142 of the shell housing 110 to lock the knife carrier 114 in the retracted position.

After the stapling procedure is completed, a clinician may want to remove a tissue donut from within the annular knife 116. When the clinician grasps the tissue donut and pulls the tissue donut distally to pull the tissue donut from the shell housing 110, engagement between the carrier springs 180 and the distal wall 186 of the recesses 154 prevents distal movement of the knife carrier 114 and the annular knife 116 to retain the annular knife 116 in a position recessed within the shell housing 110.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A reload assembly comprising:
    a shell housing including an inner housing portion and an outer housing portion, the inner housing portion spaced from the outer housing portion to define an annular cavity;
    a staple cartridge supported on a distal portion of the shell housing, the staple cartridge having a plurality of staple pockets, each of the staple pockets receiving a staple;
    a pusher assembly supported within the annular cavity, the pusher assembly movable between a retracted position and an advanced position to eject the staples from the staple cartridge;
    a knife carrier defining a longitudinal axis and supporting a knife, the knife carrier defining a stepped central bore having a distal portion and a proximal portion and including a shoulder positioned between the distal and proximal portions of the central bore; and
    at least one engagement member supported on the knife carrier, the at least one engagement member positioned to engage the inner housing portion of the shell housing when the knife carrier is in its retracted position to retain the knife carrier in its retracted position until a predetermined force is applied to the knife carrier to disengage the at least one engagement member from the inner housing portion.

2. The reload assembly of claim 1, wherein the inner housing portion of the shell housing has an outer surface defining at least one recess and the at least one engagement member is received within the at least one recess when the knife carrier is in its retracted position.

3. The reload assembly of claim 2, wherein the at least one engagement member includes a carrier spring that is supported on the shoulder of the knife carrier, the carrier spring extending across a portion of the stepped central bore and received within the at least one recess when the knife carrier is in its retracted position.

4. The reload assembly of claim 3, wherein the at least one recess includes two recesses and the at least one engagement member includes two carrier springs, each of the carrier springs being received in a respective one of the two recesses when the knife carrier is in its retracted position.

5. The reload assembly of claim 3, wherein the at least one recess defines a distal wall, the distal wall defining the at least one recess defining a wall axis, the wall axis and the longitudinal axis of the knife carrier defining an angle $\Omega$ of between 45 degrees and 85 degrees.

6. The reload assembly of claim 3, wherein the angle $\Omega$ is between 60 degrees and 75 degrees.

7. The reload assembly of claim 3, wherein the shoulder defines openings and the carrier spring includes first and second ends, each of the first and second ends positioned within one of the openings to secure the carrier spring to the shoulder of the knife carrier.

8. The reload assembly of claim 1, wherein the pusher assembly includes an annular pusher and a pushing member, the pushing member including fingers that are received within the staple pockets of the staple cartridge.

9. A circular stapling device comprising:
    an elongated body having a proximal portion and a distal portion; and
    a reload assembly supported on the distal portion of the elongated body, the reload assembly including:
    a shell housing including an inner housing portion and an outer housing portion, the inner housing portion spaced from the outer housing portion to define an annular cavity;
    a staple cartridge supported on a distal portion of the shell housing, the staple cartridge having a plurality of staple pockets, each of the staple pockets receiving a staple;
    a pusher assembly supported within the annular cavity, the pusher assembly movable between a retracted position and an advanced position to eject the staples from the staple cartridge;
    a knife carrier defining a longitudinal axis and supporting a knife, the knife carrier defining a stepped central bore having a distal portion and a proximal portion and including a shoulder positioned between the distal and proximal portions of the central bore; and
    at least one engagement member supported on the knife carrier, the at least one engagement member positioned to engage the inner housing portion of the shell housing when the knife carrier is in its retracted position to retain the knife carrier in its retracted position until a predetermined force is applied to the knife carrier to disengage the engagement member from the inner housing portion.

10. The circular stapling device of claim 9, wherein the inner housing portion of the shell housing has an outer surface defining at least one recess and the at least one engagement member is received within the at least one recess when the knife carrier is in its retracted position.

11. The circular stapling device of claim 10, wherein the at least one engagement member includes a carrier spring that is supported on the shoulder of the knife carrier, the carrier spring extending across a portion of the stepped central bore and received within the at least one recess when the knife carrier is in its retracted position.

12. The circular stapling device of claim 11, wherein the at least one recess includes two recesses and the at least one engagement member includes two carrier springs, each of the carrier springs being received in a respective one of the two recesses when the knife carrier is in its retracted position.

13. The circular stapling device of claim 11, wherein the at least one recess defines a distal wall, the distal wall defining the at least one recess defining a wall axis, the wall axis and the longitudinal axis of the knife carrier defining an angle $\Omega$ of between 45 degrees and 85 degrees.

14. The circular stapling device of claim 13, wherein the angle $\Omega$ is between 60 degrees and 75 degrees.

15. The circular stapling device of claim 11, wherein the shoulder defines openings and the carrier spring includes first and second ends, each of the first and second ends positioned within one of the openings to secure the carrier spring to the shoulder of the knife carrier.

16. The circular stapling device of claim 9, wherein the pusher assembly includes an annular pusher and a pushing member, the pushing member including fingers that are received within the staple pockets of the staple cartridge.

17. The circular stapling device of claim 9, further including a handle assembly, the elongated body being supported on the handle assembly.

* * * * *